(12) United States Patent
Schouenborg

(10) Patent No.: US 8,457,762 B2
(45) Date of Patent: Jun. 4, 2013

(54) ELECTRODE BUNDLE

(75) Inventor: Jens Olaf Roe Schouenborg, Lund (SE)

(73) Assignee: Neuroano AB, Karlshamn (SE)

(*) Notice: Subject to any disclaimer, the term of this patent is extended or adjusted under 35 U.S.C. 154(b) by 1151 days.

(21) Appl. No.: 11/543,825

(22) Filed: Oct. 6, 2006

(65) Prior Publication Data

US 2007/0088417 A1   Apr. 19, 2007

Related U.S. Application Data

(60) Provisional application No. 60/723,836, filed on Oct. 6, 2005.

(51) Int. Cl.
*A61N 1/05* (2006.01)

(52) U.S. Cl.
USPC ............................................... 607/116

(58) Field of Classification Search
USPC .......................................... 607/116, 126–128
See application file for complete search history.

(56) References Cited

U.S. PATENT DOCUMENTS

| | | | | |
|---|---|---|---|---|
| 5,179,962 A | * | 1/1993 | Dutcher et al. | ............... 607/128 |
| 5,300,110 A | * | 4/1994 | Latterell et al. | ............... 607/130 |
| 5,366,493 A | | 11/1994 | Scheiner et al. | |
| 5,931,864 A | * | 8/1999 | Chastain et al. | ............... 607/128 |
| 6,080,160 A | | 6/2000 | Chen et al. | |
| 6,171,239 B1 | | 1/2001 | Humphrey | |
| 6,181,973 B1 | * | 1/2001 | Ceron et al. | ............... 607/126 |
| 6,597,953 B2 | | 7/2003 | Boling | |
| 6,613,378 B1 | | 9/2003 | Erhan et al. | |
| 6,647,296 B2 | | 11/2003 | Fischell et al. | |
| 7,013,181 B2 | * | 3/2006 | Westlund | ...................... 607/120 |
| 7,146,226 B2 | * | 12/2006 | Lau et al. | ...................... 607/129 |
| 7,330,764 B2 | * | 2/2008 | Swoyer et al. | ............... 607/115 |
| 2003/0083724 A1 | | 5/2003 | Jog et al. | |
| 2003/0220676 A1 | * | 11/2003 | Helland | ....................... 607/122 |
| 2005/0228249 A1 | | 10/2005 | Boling | |
| 2006/0178709 A1 | | 8/2006 | Foster et al. | |
| 2007/0032717 A1 | * | 2/2007 | Brister et al. | ................ 600/347 |
| 2007/0088417 A1 | | 4/2007 | Schouenborg | |

FOREIGN PATENT DOCUMENTS

| | | |
|---|---|---|
| WO | WO-03028521 A2 | 4/2003 |
| WO | WO-03/077988 | 9/2003 |
| WO | WO-03086502 A2 | 10/2003 |
| WO | WO-2007040442 | 4/2007 |

OTHER PUBLICATIONS

William D. Memberg, et al. "An Analysis of the Reliability of Percutaneous Intramuscular Electrodes in Upper Extremity FNS Applications," IEEE Transactions on Rehabilitating Engineering, vol. 1 No. 2, Jun. 1993.

(Continued)

*Primary Examiner* — George Evanisko
(74) *Attorney, Agent, or Firm* — Dickstein Shapiro LLP

(57) ABSTRACT

An electrode bundle for implantation in soft tissue comprises two or more electrodes aligned in parallel. Each electrode comprises an electrode element, an anchoring element joined to the electrode element at a portion intermediate between the front end and the rear end thereof and a means bundling the electrodes disposed between the anchoring element and the rear end. The anchoring element forms an angle α from 0° to 6° with the electrode element and extends in the direction of the rear end thereof. Also disclosed is a stack of electrode bundles, methods for insertion of the bundle and the stack into soft tissue, and their uses.

25 Claims, 9 Drawing Sheets

OTHER PUBLICATIONS

Bhadra et al., Annals of Biomedical Engineering, vol. 25, pp. 1017-1025 (1997).

Verloop et al., Journal of Neuroscience Methods, vol. 11, pp. 173-178 (1984).

Nicolelis et al., Proceedings of the National Academy of Sciences of the United States of America, vol. 100, No. 19, pp. 11041-11046 (2003).

Yu et al., Archives of Physical Medicine and Rehabilitation, vol. 82, No. 1, pp. 20-25 (2001).

* cited by examiner

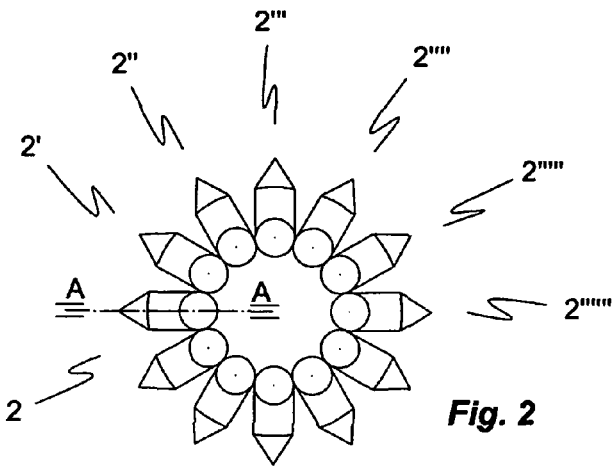
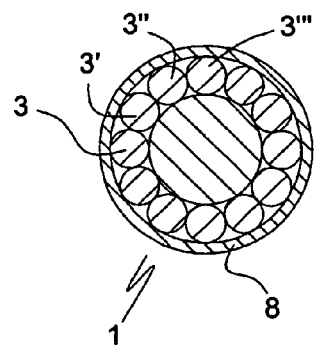
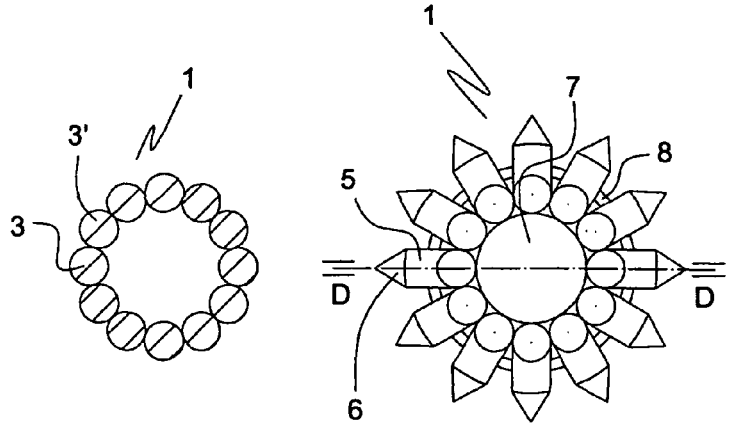
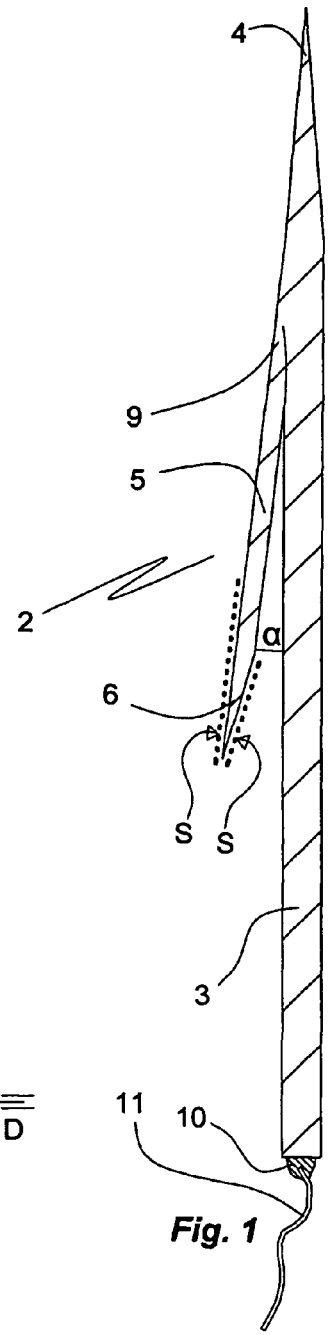
Fig. 2
Fig. 3a
Fig. 3b
Fig. 3c
Fig. 1

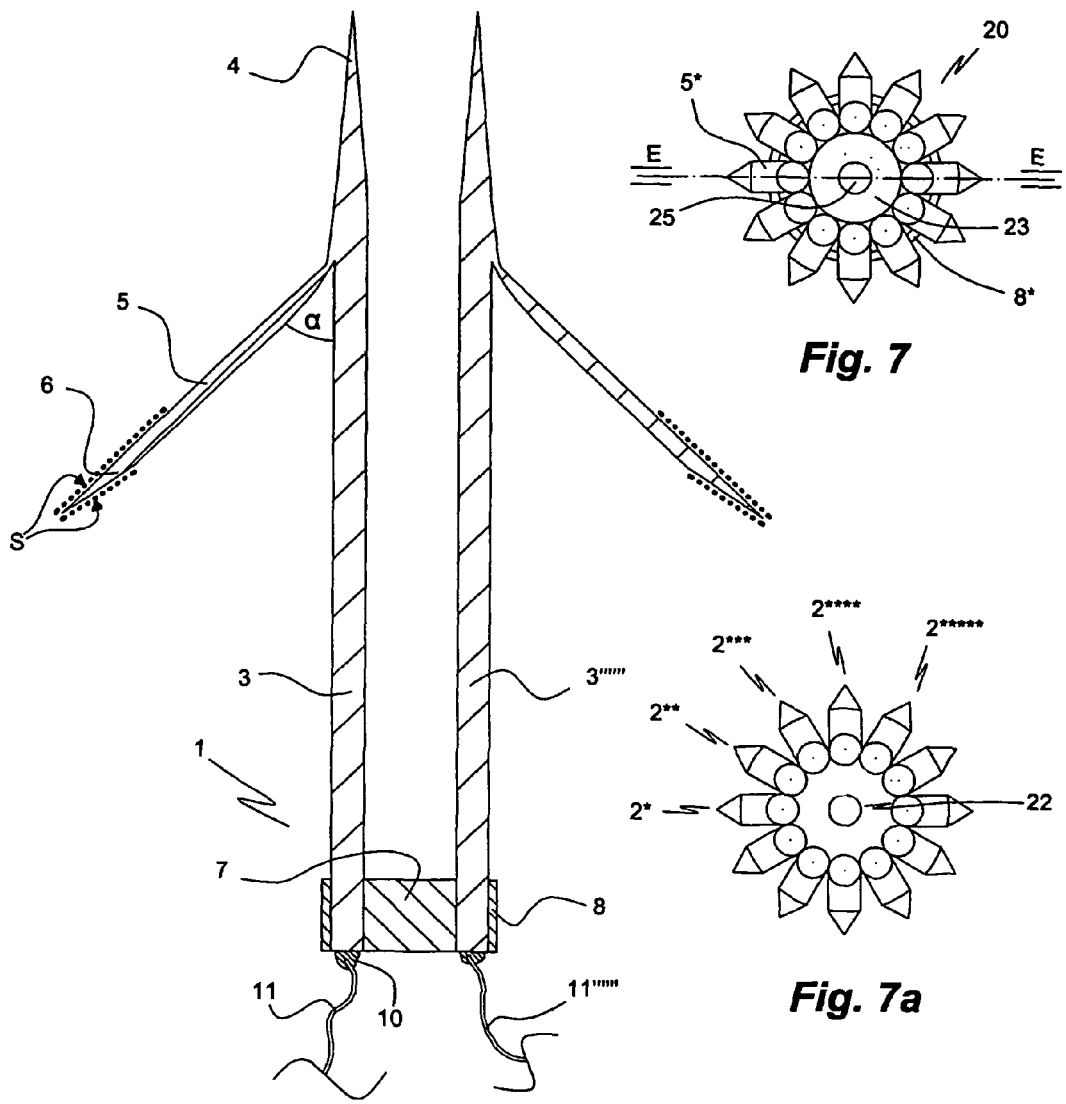

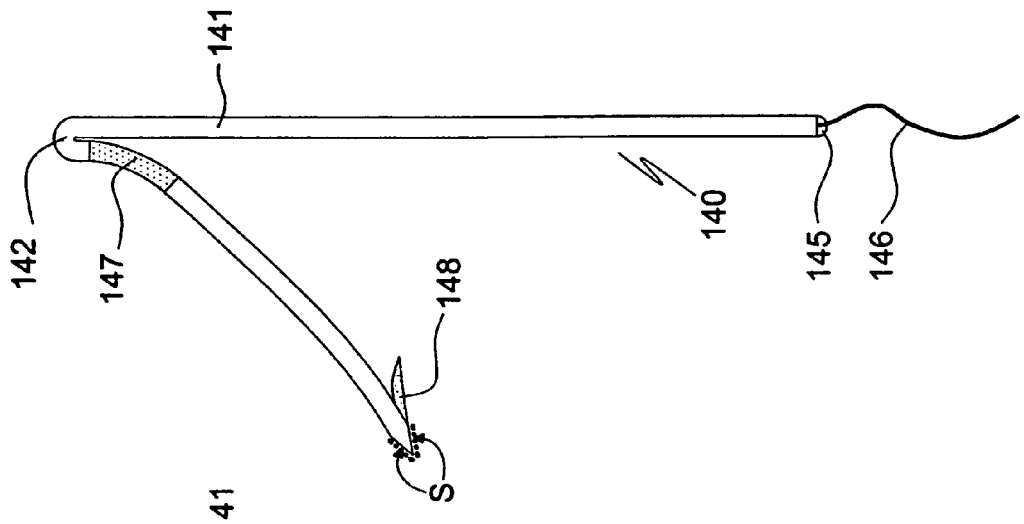
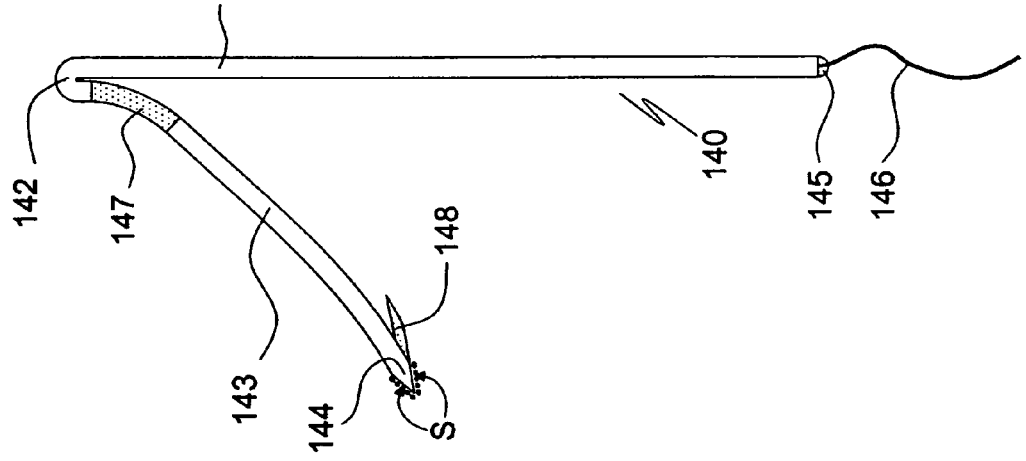
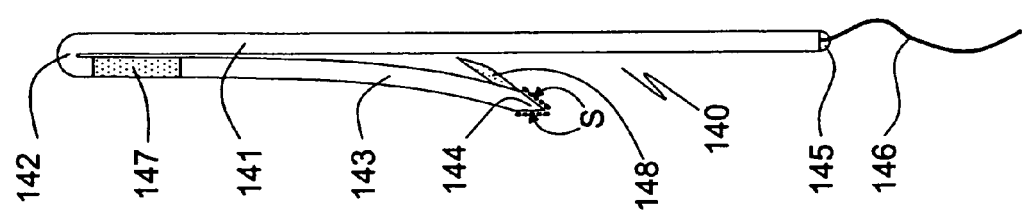
Fig. 16c
Fig. 16b
Fig. 16a

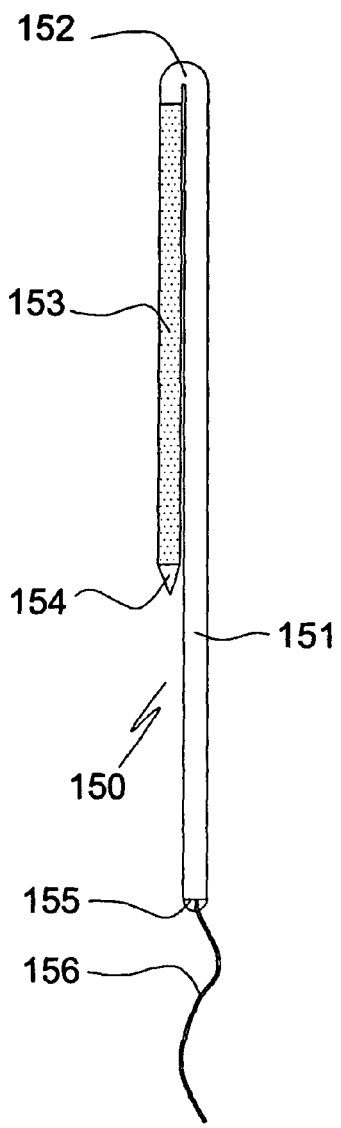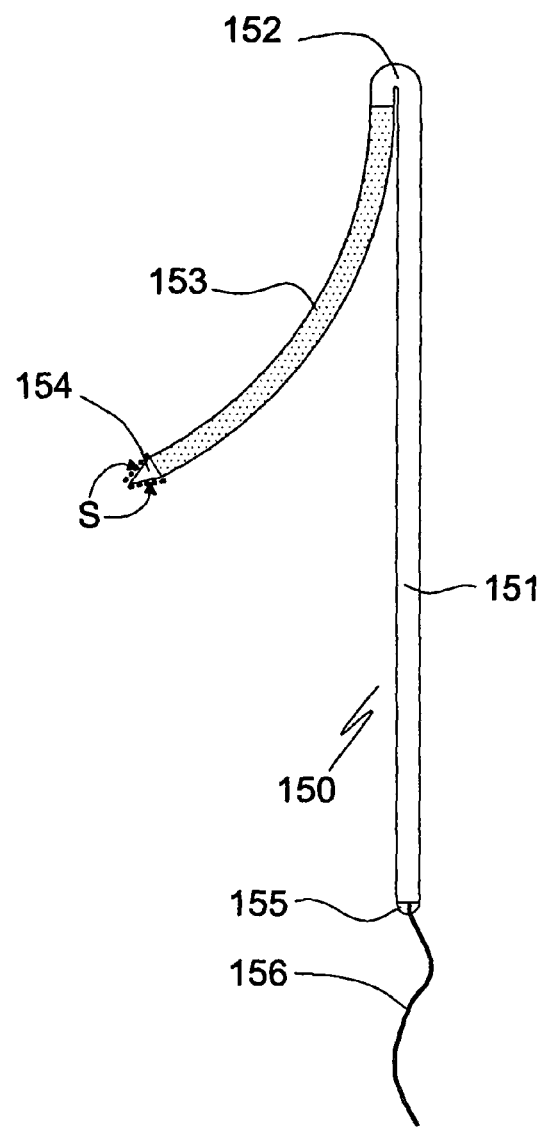
*Fig. 17a*  *Fig. 17b*

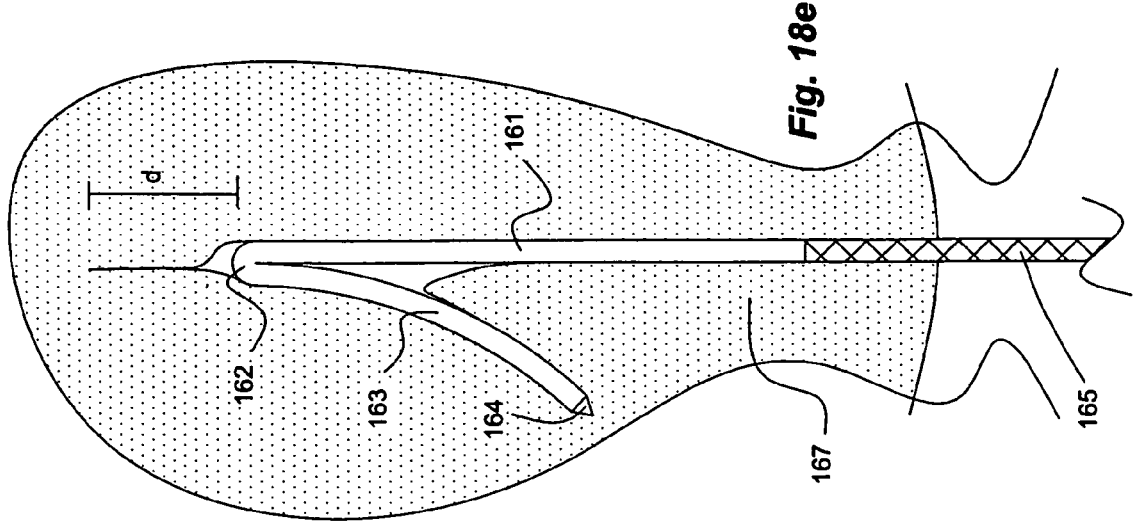
*Fig. 18e*
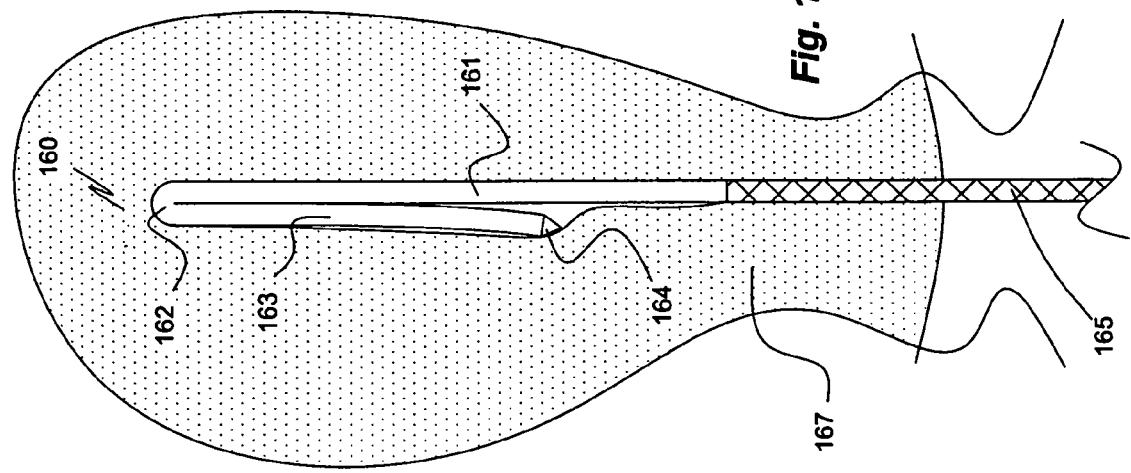
*Fig. 18d*
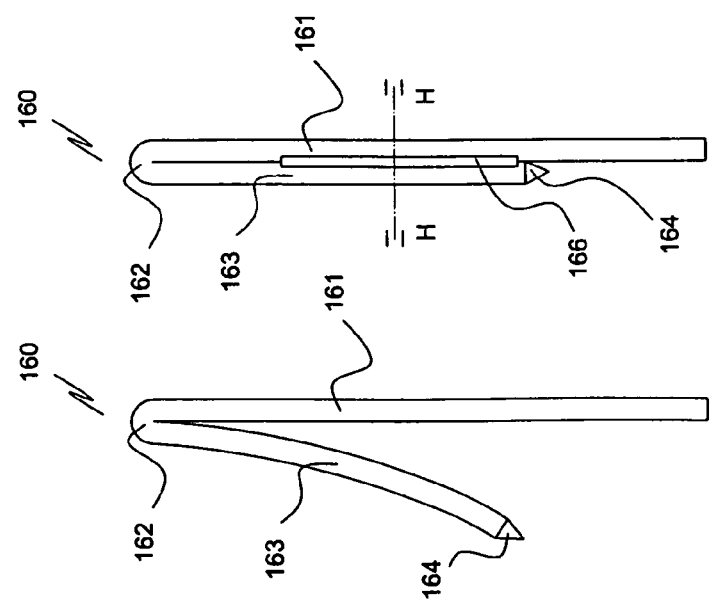
*Fig. 18a*   *Fig. 18b*
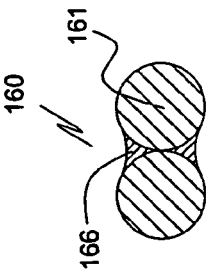
*Fig. 18c*

ELECTRODE BUNDLE

FIELD OF THE INVENTION

The invention relates to a medical electrode bundle for insertion into soft tissue such as the brain, the spinal cord, endocrine organs, muscles, and connective tissue.

BACKGROUND OF THE INVENTION

Electrodes that can be implanted for a long time into the central nervous system (CNS) have a wide application. In principle, all brain nuclei can be recorded from or stimulated by such electrodes and their functions monitored and controlled. Stimulation of the brain or spinal cord can be of particular value in situations when brain nuclei are degenerated or injured. Monitoring brain activity can be useful if linked to drug delivery or other measures such as electrical stimulation. Electrodes can also be used to lesion specific sites in tissue. To record and stimulate brain structures various forms of implanted electrodes have been developed and used in the past. For a long time implantable electrodes have been used for symptomatic treatment of Parkinson's disease (U.S. Pat. No. 6,647,296 B), chronic pain and control of spinal function.

Single relatively stiff electrodes with one or multiple sites for recording and/or stimulation disposed along their shafts (US 2003083724 A), twisted wire electrodes, multi-channel electrodes consisting of a multitude of parallel wires (WO 03077988 A, U.S. Pat. No. 6,171,239 B), multi-array needle-like electrodes (U.S. Pat. No. 6,171,239 B) protruding from a base plate are known in the literature. Known multichannel electrode arrays with electrodes protruding from a base plate consist of relatively stiff wires or needle-like electrodes that allow recordings/stimulation only in superficial parts of the brain. Further electrodes of this kind are disclosed in US 20060178709 A, US 20050228249 A, U.S. Pat. No. 5,366,493 A, and U.S. Pat. No. 6,597,953 B.

A particular problem with known electrodes of this kind is their retention at the desired site in tissue, in particular in the brain, over an extended period of time, such as from one week to one month and event for one year or more. Dislocation after insertion may make them entirely useless. For instance, implanted wire electrodes used in pain control are not equipped with anchoring means capable of retaining them in their original position close to the target cells. Consequently, they are often dislocated after insertion into brain areas that exhibit constant rhythmic movements due to breathing and heart activity, like the brain stem or the spinal cord resulting in therapy failure.

Another problem with known electrodes is damage of brain or other soft tissue caused during insertion.

Known multi-channel electrode arrays with stiff electrodes are vulnerable to tissue acceleration, for example when the patient's head is suddenly moving. The resulting shearing forces may irritate the tissue or even kill cells adjacent to the electrode. In addition, there has not been provided a solution to the problem of precisely positioning multiple ultra thin and flexible electrodes deep into the central nervous system.

OBJECTS OF THE INVENTION

One object of the invention is to provide a multi-channel electrode of the aforementioned kind that can be placed at a desired location in soft tissue and be anchored there without causing excessive damage to the tissue.

Another object of the invention is to provide a multi-channel electrode of the aforementioned kind that is retained in a chosen location in soft tissue over an extended period of time and that is not easily displaced by corporal movements of the person into which the electrode is implanted.

An additional object of the invention is to provide an electrode of this kind which additionally is easy to manufacture.

Further objects of the invention will become evident from a study of a short description of the invention, a number of preferred embodiments illustrated in a drawing, and of the appended claims.

SUMMARY OF THE INVENTION

According to the present invention is disclosed an electrode bundle of the aforementioned kind comprising two or more electrodes each comprising an electrically conducting electrode element and an anchoring element. The electrode element has a rear end and a front end. The anchoring element functions in the manner of a barb and comprises a preferably pointed tip at its one end; at its other end it is attached to the electrode element from which it extends obliquely in the direction of the rear end thereof so as to form a sharp angle $\alpha$ of 0° to 6°, and also from about 5° to about 25°. In the electrode bundle, which has a distal end and a proximal end, the two or more electrodes are aligned with their front ends defining a distal end portion of the bundle and with their rear ends defining a proximal end portion of the bundle and their electrode elements disposed about in parallel so as to make the anchoring elements to extend in proximal directions from the bundle. This arrangement makes the anchoring elements to function as barbs once the electrode bundle has been inserted into tissue, and thus to anchor the electrode bundle therein so as to prevent accidental withdrawal. This traditional kind of anchoring effect is accompanied by the important capacity of the electrode of the invention to become even better anchored if submitted to a force seeking to withdraw it from tissue. Anchoring is facilitated by the anchoring element having being curved away from the electrode element, in particular at a portion extending from the tip of the anchoring element. An attempt to withdraw an electrode inserted into soft tissue forces the anchoring element away from the electrode element, making it penetrate deeper into surrounding tissue and thus to distribute the withdrawing load over a larger volume of tissue. It is preferred for the electrodes to be coated by a non-conductive material such as a polymer or lacquer, except for at the tips of their anchoring elements.

According to an advantageous aspect of the invention the electrode bundle comprises two or more electrodes and at least one separate electrically non-conducting anchoring element comprising a rod and a barb extending from the rod in a proximal direction.

The electrode bundle of the invention may have any desired cross-section in a transverse direction, that is, a direction perpendicular to an axis extending from its distal end to its proximal end; a circular cross-section is preferred. According to a preferred aspect of the invention the electrode bundle may however also be substantially flat and have a corresponding cross-section; in such case it is preferred for it to be arranged on a flat and non-conductive support. An electrode bundle that is not substantially flat is preferably bunched at or near its distal end by means of a collar, a sleeve, a ring, an adhesive or similar. In bunching consideration should be given to the disposal of the electrode elements and the anchoring elements or the electrode elements with integrated anchoring elements so as to obtain a desired electrode bundle geometry for insertion into tissue; preferably the anchoring elements are disposed so as to extend radially outwards from the bundle in the manner of supporting ribs of an umbrella. They are preferably flexible. If they are not flexible it is preferred for them to be attached to the respective electrode element in a hinge-like manner. This will allow their free ends to be displaced radially outwards when a force acting in a proximal direction is applied to the electrode bundle, that is, to act as barbs that retain or anchor the electrode bundle in tissue.

The insulated electrical leads connected to rear portion of the electrodes by means of, for instance, a solder or electrically conducting glue are suitably housed in a common flexible tube.

According to another preferred aspect of the invention the electrode bundle comprises two or more electrodes each having one or more integral anchoring elements. The integral anchoring element(s) are conductively connected with the electrode, electric contact with soft tissue being preferably provided exclusively via the anchoring element(s), most preferred at or near their preferably pointed tips(s). If the diameter of the anchoring elements at or in close proximity of the tips is very small, such as below 2 μm, the tips can have any shape. In such case the electrode element surface and most of the anchoring element surface is covered by an insulating layer, such as a thin layer of a substantially flexible polymer material such as polyethylene or Teflon or a lacquer. It is within the scope of the present invention to increase surface of the electrode tips by, for instance, roughening, grooving, etching, etc. It is preferred to make the electrode of the invention from one piece of a thin wire with good conducting properties. The wire may be insulated from the start, and the insulation ablated at portions of the electrode that should be in electrical contact with tissue. According to an advantageous aspect of the invention the electrode wire is of a memory metal that of a transformation temperature at or slightly below body temperature; desired portions of the memory metal wire can be treated so as to change shape at or slightly below body temperature. A memory effect is particularly useful in unfolding the anchoring element of the electrode. The electrode of the invention can also have a non-conducting core of, for instance, glass fibre covered with a conducting metal layer; the metal layer can be insulated in a conventional manner by a lacquer or a polymer coat.

According to a further preferred aspect of the invention the electrode elements with integral anchoring elements or separate electrode elements and anchoring elements are bonded to one or several oblong sheets of a non-conductive material each sheet having a front end and rear end and being preferably similar in form. The electrode elements and the anchoring elements or the electrode elements with integrated anchoring elements on a sheet are disposed in parallel and with their front and rear ends in proximity of the front and rear ends, respectively, of the sheet from which long sides the barb portions of the anchoring or combined elements extend in a proximal direction. Two or more such sheets may be superimposed in a congruent manner and bonded to each other to form a layered electrode bundle. The sheets may be also wrapped around a cylinder or cone core.

The electrode bundle of the invention permits ultra thin electrodes to be inserted into and anchored in deep tissue. This substantially reduces the risk of dislocation of the electrodes due to tissue movements. To further improve anchoring properties, the barb element surface may be rough or have adhesive properties. The electrically insulating layer or coating on the electrodes may be given a rough or uneven surface. The coating should preferably be biocompatible and/or be covered by a biocompatible material such as a polysaccharide to facilitate insertion into tissue and/or improve anchoring properties by attached hydrophobic groups, for instance be silanized. The use of coating materials that reduce scar formation is also preferred.

The electrode bundle of the invention provides a means for electrical stimulation of soft tissue over an extended period of time, such as a month or more and even one or several years. Electrical pulses of desired shape and length can be generated in a control unit to which the electrode leads are connected. Additionally the electrode bundle of the invention provides a means for sampling electric signals generated by the human or animal body, such as signals produced by neurones, or sampling electrochemical signals from intra- or extra cellular fluids. The electrode bundle can be used for a number of therapeutic purposes, such as pain control, treatment of Parkinson's disease and epilepsy, boosting of memory, and mood control.

Particularly advantageous is a rotationally symmetric electrode bundle of the invention similar in form to the skeleton of an umbrella. For reasons of simplicity, this rotationally symmetric electrode bundle may be termed "umbrella electrode". The umbrella electrode of the invention allows a large set of very small and delicate electrodes, such as electrodes with a diameter in the nanometer or lower micrometer range, to be inserted into a brain structure. The umbrella electrode is inserted into tissue in a folded state and anchored there by an unfolding movement. The umbrella electrode may comprise hundreds and even thousands of electrode elements and, once disposed and anchored in the brain, be capable of serving as a stimulating or recording device addressing numerous of neurons/small groups of neurons. The umbrella electrode may also be implanted in any other soft tissue.

The invention will now be explained in more detail by reference to preferred embodiments of the invention illustrated in a rough drawing, which, for clarity reasons, is not to scale; most transverse dimensions are greatly exaggerated.

DESCRIPTION OF THE DRAWING

FIG. 1 is an axial section A-A (FIG. 2) of an electrode of the electrode bundle of the invention;

FIG. 2 is a top view of an array of 12 electrodes of an electrode bundle of the invention, disposed in the same manner as in the bundle;

FIGS. 3a and 3b are transverse sections B-B and C-C (FIG. 4), respectively, of a first embodiment of the electrode bundle of the invention;

FIG. 3c is a top view of the electrode bundle of FIGS. 1 and 2, in a folded state;

FIG. 5 is an axial section corresponding to that of FIG. 4 of the electrode bundle, in an unfolded state;

FIG. 7 is a top view of the electrode bundle of FIG. 6, in the same state;

FIG. 7a is a top view of the electrodes of the electrode bundle of FIGS. 6 and 7, in the same view and disposition as in FIG. 7;

FIGS. 16a-16c are side views of still another embodiment of an electrode of the electrode bundle of the invention, in a folded state (16a) and an unfolded state (16b and 16c), comprising a further anchoring element shown in a folded state in FIGS. 16a and 16b, and in an unfolded state in FIG. 16c;

FIGS. 17a and 17b a side views of a further embodiment of an electrode of the electrode bundle of the invention, in a folded state (17a) and an unfolded state (17b) comprising an anchoring element of memory metal;

FIGS. 18a and 18b, are side views and FIG. 18c is a sectional view H-H of an additional embodiment of an electrode of the electrode bundle of the invention, which is shown in FIGS. 18d and 18e in two phases of insertion into tissue and anchoring.

DETAILED DESCRIPTION OF THE INVENTION

Example 1

Figure 4:
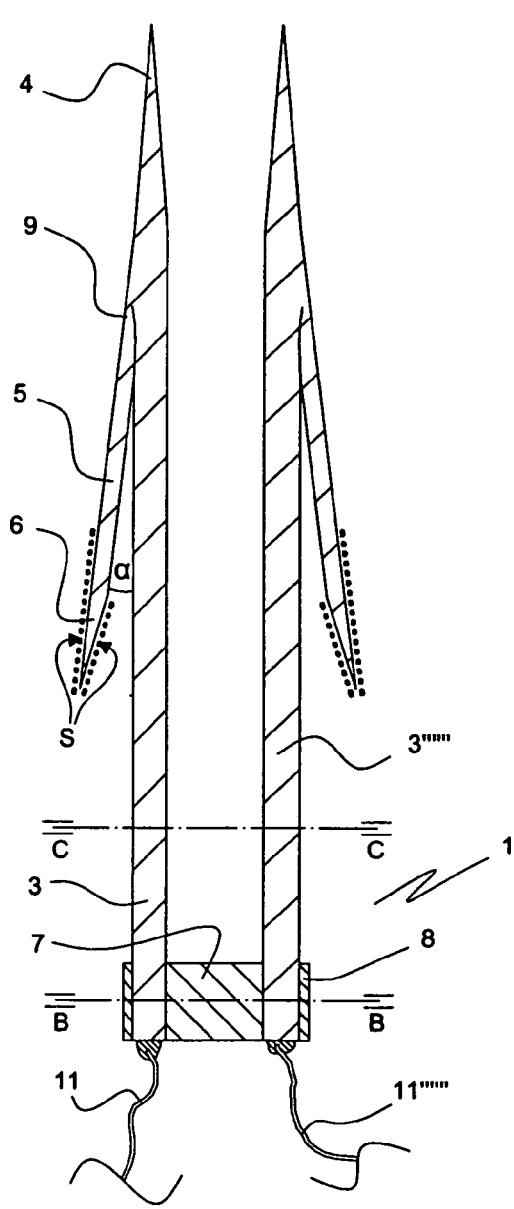
FIG. 4 is an axial section D-D (FIG. 3c) of the electrode bundle, in a folded state.

Preferred embodiments of the electrode bundle of the invention. FIGS. 1 to 5 illustrate a first embodiment of the electrode bundle of the invention in form of an umbrella electrode 1. The umbrella electrode 1 comprises twelve like electrodes 2, 2', 2", 2''', 2'''', 2''''', 2'''''', etc. An electrode 2 comprises a cylindrical electrically conducting electrode rod 3 having a tip 4 at its one (front) end. An integral anchoring element or barb 5 having a tip 6 at its free end extends in a skew rearward fashion from a section of the electrode rod 3 near the tip 4 in the direction of the blunt distal end of the electrode rod 3, to which a thin insulated wire 11 is attached by a solder 10. The electrode rod 3 and the barb 5 are made of a good conductor such as platinum, silver, gold, copper, their alloys and other suitable metals and alloys; carbon fibres and fibres of electrically conducting polymers may also be used. The electrode element 3 and the barb 5 can also be made of a core of non-conductive material, such as glass or polymer covered by a conductive material such as metal. If the electrode 3 and the barb 5 have a core of non-conductive material covered by a layer of conductive material such as a metal, their preferred diameter is the same as for electrodes made of electrically conductive wire. If the electrode element 3 and the barb 5 is made of metal wire their diameter is preferably from about $10^{-4}$ m to $10^{-7}$ m. A particularly preferred diameter is from $1\times10^{-6}$ m to $25\times10^{-6}$ m. Except for at their tips 4, 6 the electrode element 3 and the barb 5 are cylindrical. In an unfolded state (FIGS. 1 to 4) their axes (not shown) include a sharp angle α of about 100°. At the region of attachment of the barb 5 to the rod 3 the diameter of the former narrows, which makes the barb 5 more flexible in that region than otherwise, so as to provide a hinge function. Except for its tip 6 the barb 5 and the electrode rod 3 is electrically insulated by a thin layer of polymer such as Teflon or polyethylene or by a lacquer. This is not shown in the Figures; the non-insulated tip 6 portion is indicated by dotted lines S extending along it. The insulating coating can have a roughened surface (not shown) to improve the anchoring properties of the barb 5.

The umbrella electrode 1 is assembled by disposing the twelve electrodes 2', 2", 2''', 2'''', 2''''', 2'''''', etc. along the periphery of a circle of a size to allow the rods 3, 3', 3", etc. of neighbouring electrodes to abut each other and with the axes of the barbs 5, 5', 5", etc extending in an axial direction in respect of the circle. This disposition is shown in FIG. 2. For forming a physically stable electrode bundle, that is, the umbrella electrode 1, the electrode rods 3, 3', 3", etc. are disposed along the periphery of a short cylinder 7 of same diameter (FIG. 3a). In this disposition the electrodes 2', 2", 2''', 2'''', 2''''', 2'''''' are mounted by clamping them to the cylinder 7 by means of a sleeve 8. The cylinder 7 is of stiff polymer material such as polycarbonate whereas the sleeve is of a thermosetting polymer such as polypropylene. It is within the ambit of the invention to use electrodes with electrode rods 3 and/or barbs 5 of different length in a single electrode bundle. A disposition of electrode rods 3 that is not rotationally symmetrical is also comprised by the invention. The correctly disposed electrodes 2 can also be mounted by gluing, in which case the mounting cylinder 7 and sleeve 8 can be dispensed with.

The umbrella electrode 1 of FIGS. 1-5 is inserted into tissue in the configuration of FIG. 4, in which the barbs 5, 5', 5", etc. form a sharp angle α, such as one of about 10°, with the respective electrode rods 3, 3', 3", etc. After the desired depth of insertion is reached slight withdrawal of the umbrella electrode 1 in a proximal direction makes the barbs 5, 5', 5", etc. rotate at their restrictions 9 that function in a hinge-like manner. The umbrella electrode 1 thereby unfolds while the tips 6, 6', 6", etc. of the barbs 5, 5', 5", etc. move radially outwards and thereby are inserted into the tissue surrounding the electrodes 2', 2", 2''', 2'''', 2''''', 2'''''', etc. and anchored against further withdrawal. By the controlled withdrawal movement over a short distance the angle α is widened from about 10° to about 30° to about 60° and even up to 90°. Attempts to withdraw the electrode bundle 1 even more meets increased resistance. After point of maximum resistance is reached the electrodes 2', 2", 2''', 2'''', 2''''', 2'''''', etc. will eventually swing backwards to allow the electrode bundle 1 to be easily withdrawn from tissue.

Figure 6:
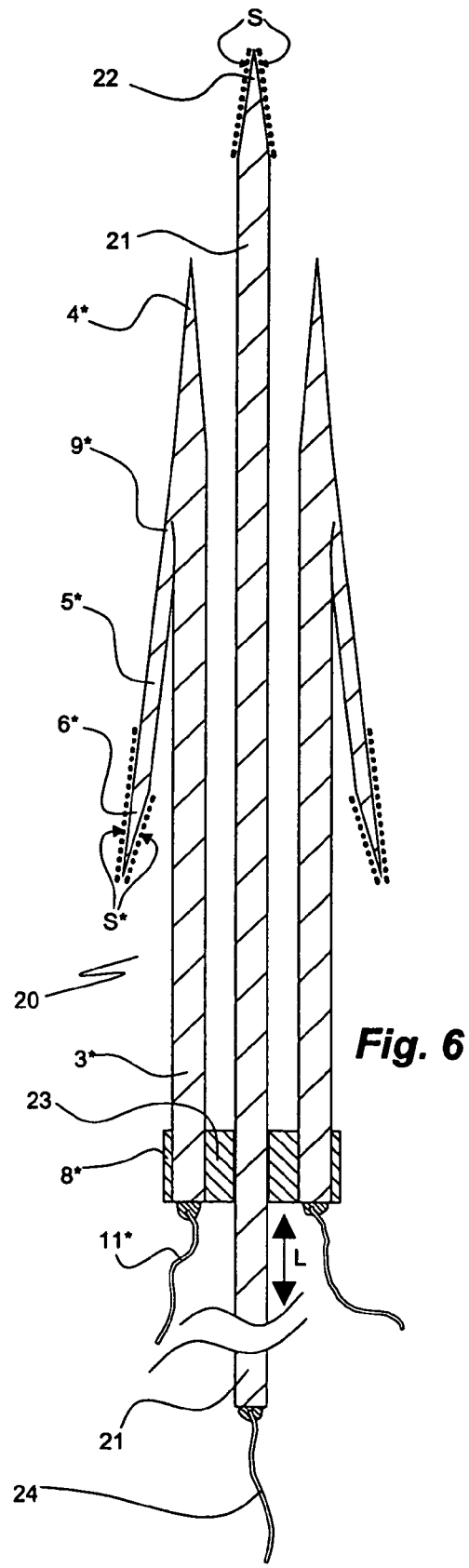
FIG. 6 is an axial section E-E (FIG. 7) of a second embodiment of the electrode bundle of the invention, in cooperation with a sensing electrode, in the same view and state as the electrode bundle in FIG. 4.

The umbrella electrode 20 of FIGS. 6, 7, and 7a corresponds substantially to the umbrella electrode 1 of FIGS. 1-5 but cooperates with a central sensing electrode 21 with a non-insulated tip 22 for monitoring insertion into tissue to a desired depth guided by electrical signals emanating from nerve synapses and neurones. Elements of the umbrella electrode 20 corresponding to those of the electrode 1 retain the numbering of the later with an asterisk; the cylinder 23 along the periphery of which the electrodes 2*, 2, 2*, etc. are mounted has a central bore 25 in which the sensing electrode 21 is snugly mounted displaceably in a distal/proximal direction as indicated by double arrow L in FIG. 6. Insertion, anchoring, and withdrawal parallels that of electrode 1 except for that the sensing electrode 21 is inserted first to find the correct depth of insertion for the electrode bundle 20. The electrode bundle 20 is then inserted to the correct depth by sliding it along the sensing electrode 21, and anchored in that position by a slight displacement in the opposite direction. Insertion of the electrode bundle 20 to the correct depth is facilitated by distance marks (not shown) printed on the sensing electrode 21, which can be completely withdrawn after insertion of the bundle 20 to the desired depth.

Figure 10:
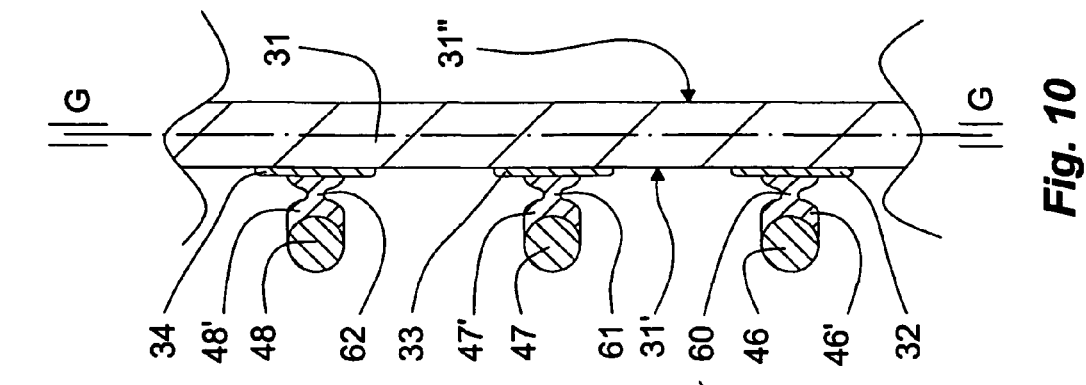
FIG. 10 is an enlarged partial sectional view F-F (FIG. 9) of the electrode bundle of FIGS. 8 and 9, seen in direction R (FIG. 9)
Figure 9:
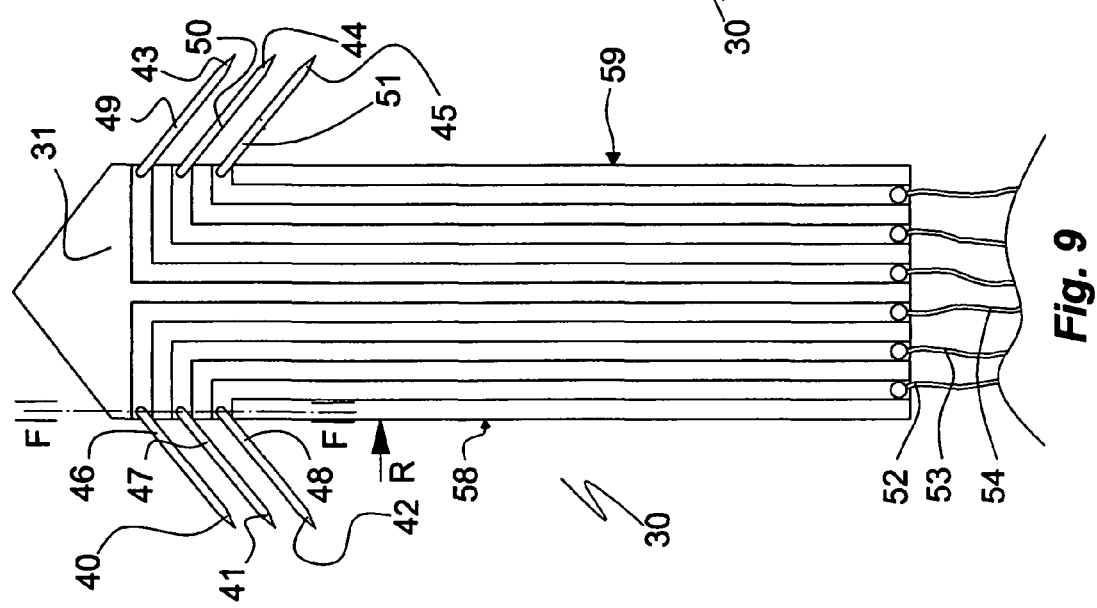
FIG. 9 is the flat electrode bundle of FIG. 8, in the same view and in an unfolded state.
Figure 8:
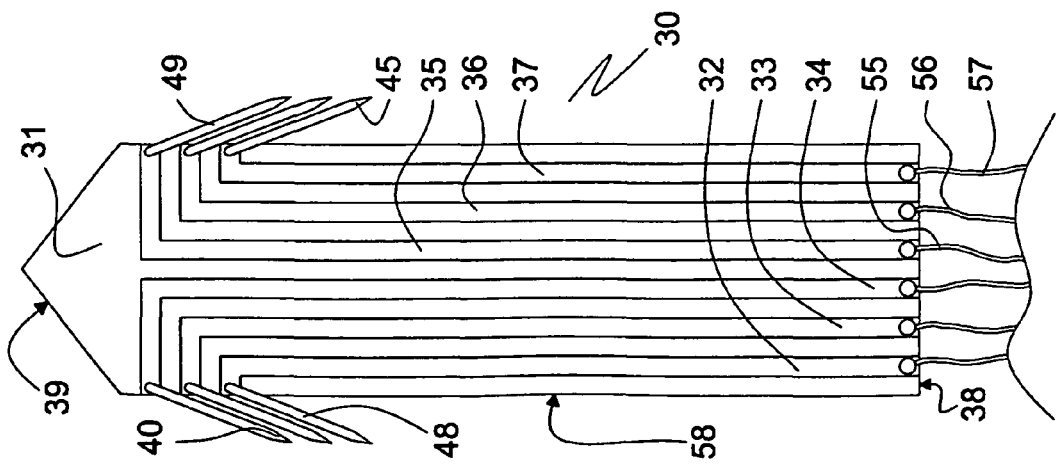
FIG. 8 is a top view of a flat third embodiment of the electrode bundle of the invention, in a folded state.

In contrast to the umbrella electrodes 1 and 20 the electrode bundle 30 of the invention illustrated in FIGS. 8-10 is substantially flat; it comprises six electrodes and retains important anchoring features of the umbrella electrodes 1 and 20. Of the faces 31', 31" of a flat non-conductive polycarbonate support 31, which may have smooth or a dimpled surface, one 31' carries a pattern of six electrodes, comprising L-formed leads 32, 33, 34, 35, 36, 37 with short base portions 32', 33', 34', 35', 36', 37' prepared by micro lithographic etching from a thin metal layer bonded to face 31' or by screen printing a thin conducting layer onto that face. The L-formed leads 32, 33, 34, 35, 36, 37 extend from the proximal or rear end 38 of the support 31 to close to its distal or front pointed end 39 and from there, in a mirroring manner, to either long side 58, 59 of the support 31 by their short bases 32', 33', 34', 35', 36', 37'. The combination lead/base combination 32/32', 33/33', 34/34', etc. forms an electrode. Close to their free ends the bases 32', 33', 34', 35', 36', 37' carry pointed cylindrical anchoring elements 46, 47, 48 and 49, 50, 51 extending in a skew proximal direction. The leads 32, 33, 34, 35, 36, 37 and, except for their pointed tips 40, 41, 42, 43, 44, 45, the anchoring elements 46, 47, 48, 49, 50, 51 are covered with a thin layer of insulating polymer. At their proximal ends each of the leads 32, 33, 34, 35, 36, 37 has a thin insulated metal wire 52, 53, 54, 55, 56, 57 attached by soldering. Upon inserting the electrode bundle 30 of FIG. 8 into soft tissue such as brain tissue to a desired depth withdrawal for a short distance makes the anchoring elements 46, 47, 48, 49, 50, 51 to slightly rotate in a plane parallel with the support 31, thereby being inserted into and anchored in the tissue surrounding the electrode bundle 30. Rotation of the anchoring elements is facilitated by constrictions 60, 61, 62, etc. (FIG. 10) in short end portions 46', 47, 48', etc. of the anchoring elements 46, 47, 48, etc. set off by 90° by which end portions the anchoring elements 46, 47, 48, etc. are joined to the respective leads 32, 33, 34, etc. To facilitate insertion into tissue the front end 39 of the support 31 is pointed.

Figure 11:
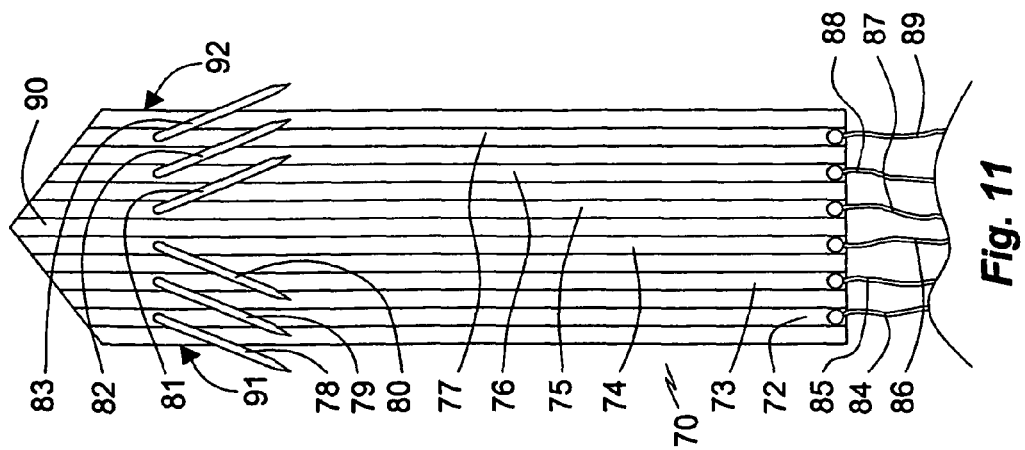
FIG. 11 is a variation of the electrode bundle of FIGS. 8-10, in the same view and in an unfolded state.

The electrode bundle 70 of the invention illustrated in FIG. 11 differs from that of FIGS. 8-10 in that leads 72, 73, 74, 75, 76, 77 do not have bases extending to either of the long sides 91, 92 of the support 90 but are extending straight from the rear end to the pointed front end. The anchoring elements 78, 79, 80, 81, 82, 83 are attached to the leads 72, 73, 74, 75, 76, 77 in a manner so as to space them equidistantly over the entire width of the oblong support 90, one half 78, 79, 80 pointing, in a skew proximal direction, towards one long side 91, the other half 81, 82, 83 in a mirroring manner to its other long side 92. In this embodiment the flexible and insulated wires soldered to the proximal ends of the leads 72, 73, 74, 75, 76, 77 are numbered 84, 85, 86, 87, 88, 89.

Figure 12:
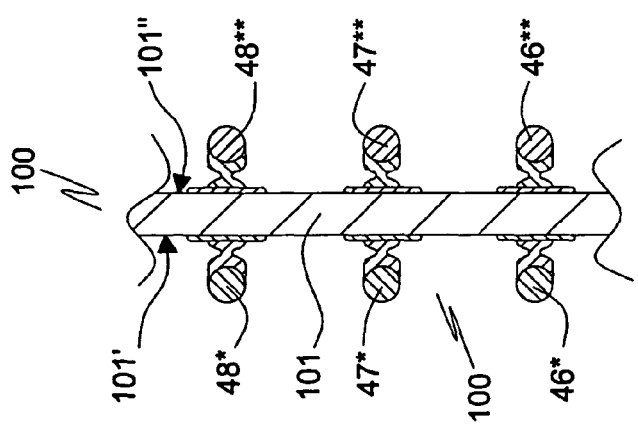
FIG. 12 is a partial sectional view of a variation of the embodiment of the flat electrode bundle of FIGS. 8-10, in a section corresponding to section E-E in FIG. 9 and in a folded state.

The electrode bundle 100 of FIG. 12 differs from the embodiment of FIGS. 8 to 10 in that the elements disposed on one face 31' of the support 31 of the embodiment of FIGS. 8 to 10 have been duplicated on the other face in a mirroring manner (mirror plane G-G in FIG. 10). The electrode bundle 100 thus is provided with electrodes on both faces 101', 101" of its support 101. The elements copied from the embodiment of FIGS. 8 to 10 retain their reference numbers but provided with one asterisk (elements on the original face 101') or two asterisks (elements on the mirrored face 101").

Figure 13:
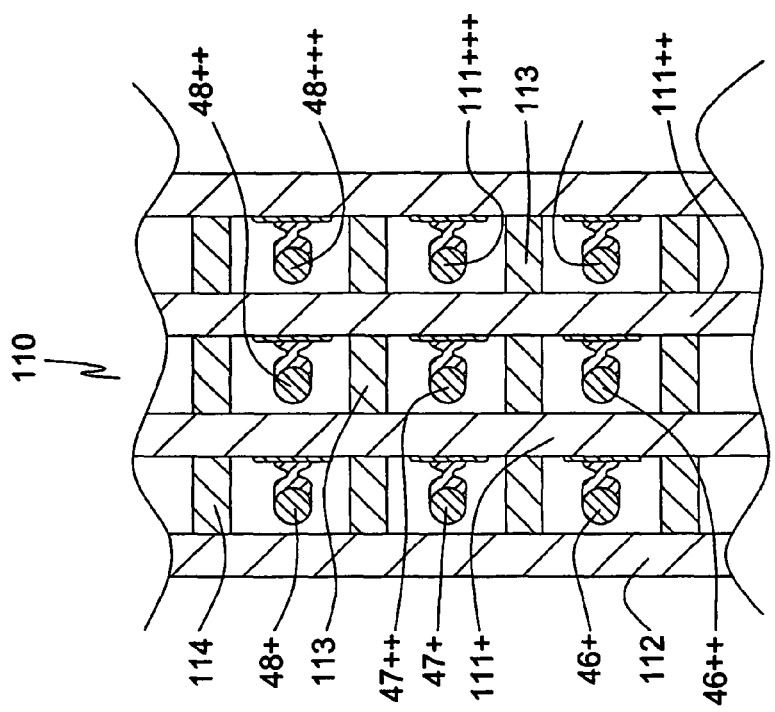
FIG. 13 is a stacked embodiment of the electrode bundle of FIGS. 8 to 10, in a section corresponding to section F-F in FIG. 9 and in a folded state.

The stacked electrode bundle 110 of FIG. 13 is obtained by superposition of three flat electrode bundles of the kind shown in FIGS. 8-10. The electrode bundle 110 has three layers of electrodes, a first layer comprising anchoring elements $46^+$, $47^+$, $48^+$, etc. and corresponding leads on a support $111^+$, a second layer comprising anchoring elements $46^{++}$, $47^{++}$, $48^{++}$, etc. and corresponding leads on support $111^{++}$, and a third layer comprising anchoring elements $46^{+++}$, $47^{+++}$, $48^{+++}$, etc. and corresponding leads on support $111^+$. The layers are kept apart by cylindrical spacers 113. A cover 112 that protects the first layer is spaced from that layer by cylindrical spacers 114. The insulating coat (not shown) of one or more electrode layers of the electrode bundle can be optionally covered by a shielding coat, such as a thin metal coat, to minimize crosstalk between electrodes of different layers. The shielding coats can be in electric contact with each other and grounded.

Figure 14:
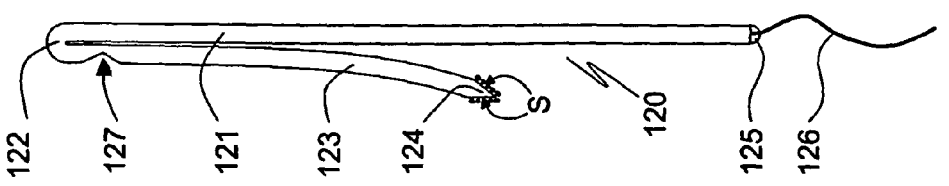
FIG. 14 is a further embodiment of an electrode of the electrode bundle of the invention, in a side view.

The embodiment 120 of the electrode of the invention shown in FIG. 14 is formed from one piece of metal wire. The barb 123 is joined to the electrode rod 121 by a 180° bend 122 forming the blunt tip of the electrode 120. At its free end the barb 123 has a sharp point 124. At its rear end an insulated flexible lead 126 is attached to the electrode rod 121 by a solder 125. Near the bend 122 the barb 123 carries a notch 127. When a force seeking to move the barb 123 away from the rod 121 is applied to the barb it will bend at the notch 127, which thus has a hinge-like function. The angle of the notch may be used to control the angle of the hinge-like function. Seen in the direction of the electrode rod 121 the barb 123 is slightly bent in a convex manner, which facilitates insertion into surrounding tissue while keeping damage to the tissue at a minimum. Except for its sharp tip 124 the electrode 120 is covered by a thin layer of insulating polymer material; the free electrode surface at tip 124 is indicated by dotted lines S extending parallel to it.

Figure 15B:
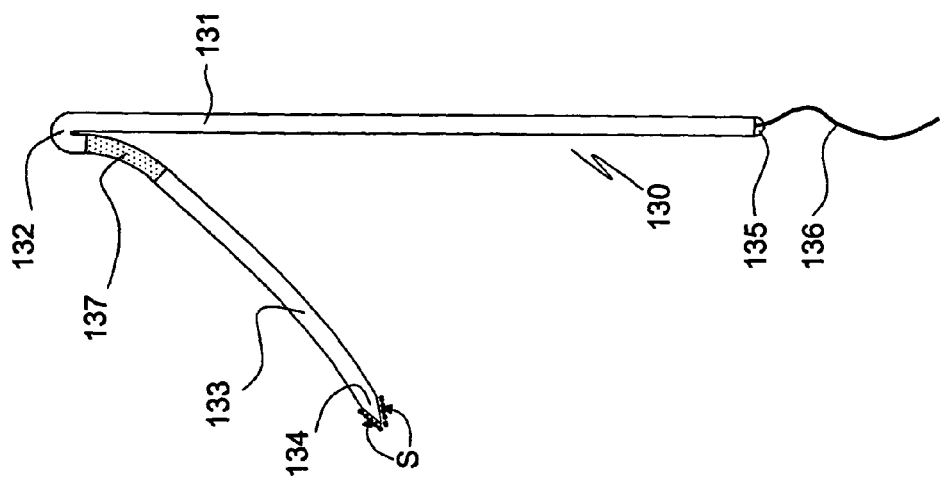
FIGS. 15a and 15b are side views of another embodiment of the electrode bundle of the invention, in a folded state and an unfolded state, respectively.
Figure 15A:
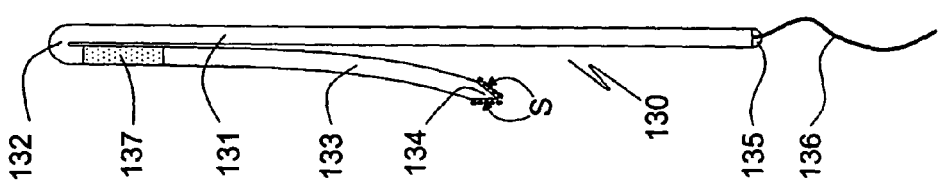

In the embodiment of an electrode 130 of the electrode bundle of the invention of FIGS. 15a and 15b the hinge means allowing unfolding of the anchoring element 133 is accomplished by providing the anchoring element 133 with a section 137 of lower resistance against a bending force by, for instance, annealing the anchoring element 133 except for its section 137. Elements 131, 132, 134, 135, and 136 have the same meaning as elements 121, 122, 124, 125, and 126 of the embodiment of FIG. 14; S in combination with dotted lines again denotes that the surface of anchoring element point 134 is not insulated.

In the embodiment of an electrode 140 of the electrode bundle of the invention of FIGS. 16a-16c the anchoring element 143 is provided with a barb 148 near its point 144 that again lacks insulation, as indicated by S in combination with dotted lines. The electrode 140 is made from one piece of a memory metal wire. Sections of the wire can be mechanically and thermally treated so as to make them to change physical shape at certain temperatures. An anchoring element section 147 close to the point where the anchoring element 143 is joined to the bend 142 at the top end of the electrode rod 141 has been treated in a manner to make it, on insertion of the electrode into tissue of 37° C., change shape; the memory effect makes the anchoring element 143 bend away from the electrode rod 141 to assume the shape shown in FIG. 16b. Close to its point 144 the anchoring element 143 has a barb 148, which has been treated so as to provide it with a memory making it bend away from the anchoring element 143 on warming. The electrode 140 thereby assumes the conformation shown in FIG. 16c. The barb 148 provides the electrode 148 with an additional anchoring effect. In the embodiment of FIGS. 16a-16c, the memory effect of the anchoring element 143 and the barb 148 differ in that the former returns faster to its stable configuration at body temperature of the barb 148. It is however within the scope of the invention and also preferred that both sections 147, 148 return to their stable configuration at the same rate. Elements 145, 146 are functionally identical to elements 125 and 126, respectively, of the embodiment of FIG. 14. S in combination with dotted lines again denotes that the surface of anchoring element point 144 is not insulated.

The anchoring element 153 of the electrode 150 of the electrode bundle of the invention of FIGS. 17a and 17b is of a memory metal having a transition temperature of about 33° C. to 35° C. In the folded state (FIG. 17a) the memory metal is in a strained, substantially straight state. Upon insertion into tissue the memory metal warms up to the transition temperature, at which the metal seeks to return to its unstrained curved state (FIG. 17b). Movement of the pointed 154 end of the anchoring element 153 away from the electrode element 151 is however impeded by surrounding tissue. A slight withdrawal of the electrode 150 in a proximal direction allows the anchoring element to unfold and thus anchor the electrode 150 in tissue. Reference numbers 152, 155, and 156 have the same meaning as reference numbers 142, 145, and 146 in FIGS. 16a-16c.

The anchoring element 163 of the electrode 160 of the invention of FIGS. 17a and 17b is resiliently flexible whereas the electrode element 161 is stiff. FIG. 18a shows the electrode 160 in an unrestrained state. In FIGS. 18b and 18c the anchoring element 163 has been forced towards the electrode element 161 so as to abut it, and has been attached in this resiliently strained state to the electrode element 161 by means of a biocompatible adhesive 166, which is water soluble or swellable; if swellable it substantially looses its adhesive properties when swollen. The adhesive 161 is of a kind that it does not dissolve or substantially swell immediately on contact with water. The time required for dissolution or swelling of the adhesive in an aqueous environment to a degree that the anchoring element 163 is released from abutment to the electrode element 161 by the resilient force of the anchoring element 163 can be suitably varied, such as from a few seconds to one or two minutes and even more. This allows the electrode 160 to be inserted into tissue to a desired depth before the anchoring element 163 comes off. Suitable biocompatible adhesives include saccharose, gelatine, gelatine derivatives, fibrin tissue glue, cellulose derivatives, modified starch, and collagen gel. The adhesive 166 is applied to the anchoring element 163 held in abutment with the electrode element 161 as an aqueous solution or gel. The solution or gel then is dried on the electrode 160. Drying can be accelerated by gently heating the solution or gel up to the boiling temperature. The dissolution or swelling rate of the adhesive 166 can be set by varying the drying or heating time and/or the temperature. With saccharose adhesive dissolution times below and above 1 min can be easily achieved by, for instance, heating the solution or gel for a selected period of time. After insertion into tissue 167 by means of a micromanipulator 165 and dissolution or swelling of the adhesive 166 the state shown in FIG. 18d is reached. The micromanipulator 167 comprises releasable means for coupling with the electrode 160, which are however not shown in the Figures. A portion of the electrode 163 extending from the tip 164 has come off the electrode element 161. Its further displacement away from the electrode element 161 is however barred by surrounding soft tissue 167. Withdrawal of the electrode 160 for a short distance d in a direction opposite to the insertion direction makes the point 164 of the anchoring element 163 penetrate the surrounding tissue 167 so as to "unfold" the anchoring element 163 and make it adopt the substantially unstrained state in FIG. 18e. For reasons of simplicity the principle of insertion into and anchoring in soft tissue 167 of a single electrode 160 is visualized in FIGS. 18d and 18e rather than insertion and anchoring of an electrode bundle comprising two or more of such electrodes 160; electrodes 160 when bundled will behave in essentially the same manner. The embodiment of FIGS. 18a to 18e can also be carried out with an electrode element that is not stiff, in particular with one that is resiliently flexible. In such case it is preferred that the portion of the electrode element of equal length as and facing the anchoring element has a bent configuration mirroring that of the anchoring element; if both elements are made of the same piece of wire the resulting electrode will have a straight configuration in the twofold strained state corresponding to that of FIGS. 18b and 18c. In FIGS. 18a-18e the flexible electrical lead attached to the rear end of the electrode element 161 is not shown.

Example 2

Positioning the Electrode Bundle in Tissue.

For optimal performance of the electrode it is critical to place it with high precision in the target tissue, in particular neuronal tissue. Since the size of the brain and spinal cord and the relative size and location of their various regions varies considerably between individuals, coordinate guided insertion is not sufficiently accurate. Preferably a 'tracking' procedure is used to locate the coordinates of the brain or spine region of interest. In this procedure the correct coordinates are determined by multiple recording/stimulation traces with single electrodes. They may also be determined by tracking by means of a guiding electrode like the guiding electrode 21 of the embodiment of FIGS. 6 and 7. Once the correct coordinates are determined they can be used to guide the insertion of the electrode bundle into the brain. The electrode bundle can be introduced into tissue by means of a micromanipulator capable of temporarily holding it at or near its rear or proximal end. The electrode bundle may be equipped with attachment means for co-operation with the micromanipulator. For example, the attachment means comprises one or several bores in the base or in the support of the bundle, respectively, into which the corresponding numbers of bars disposed at the front or distal end of the micromanipulator are inserted. Alternatively the sleeve or the support of the electrode bundle is clamped by arms of the micromanipulator during insertion and released upon deposition at the desired depth. The micromanipulator is then withdrawn.

In case of erroneous positioning the electrode bundle of the invention can be simply withdrawn; the hinge-like connection of the barb portion(s) to the anchoring element base or electrode element allows the former to swing backwards on withdrawal with minimal tissue damage. Alternatively the electrode bundle is coated in a folded state by a substrate dissolvable in body fluids, such as a polysaccharide or gelatin. Thereby the barbs are prevented from unfolding until the polysaccharide or gelatine has dissolved, allowing the umbrella electrode to be withdrawn from an erroneous position during a short period of time from insertion. Withdrawal of the electrode bundle of the invention for an appropriate short distance after dissolution of the dissolvable substrate anchors it in the tissue. According to a preferred aspect of the invention the unfolded electrode bundle coated with a dissolvable substrate comprises a guide electrode disposed in the centre of the bundle and which is insulated except at its distal tip and not provided with a barb element. During insertion the guide electrode is exclusively used for stimulation and recording of electrical signals to determine the desired location in tissue.

Example 3

Electrical Control of/Recording of Electrical Signals by the Electrode Bundle.

For an electrode of the invention intended for signal recording purposes, the electrode elements are electrically connected to a signal amplifying unit comprising an amplifying circuit and, optionally, a transmitter for wireless connection to a control unit. To avoid loss of signal strength the amplifying unit with the transmitter is disposed close to the electrode bundle. For transmission over a short distance, such as up to about 20 cm, a miniaturized first transmitter may be mounted at the rear portion of the bundle, that is, at a portion extending from the spinal cord or brain tissue, transmitting the signals to a transfer unit comprising a receiver and a second transmitter. The transfer unit may be implanted in soft tissue and comprise a wirelessly rechargeable battery.

An electrode of the invention intended for stimulation is connected to a preferably telemetrically controlled stimulating unit. Telemetric control is exerted by a control unit comprising a control circuit and a transmitter. The recording, stimulating, and signal transfer units are preferably powered by a small rechargeable battery.

Example 4

Field of Application.

The electrode bundle of the invention is primarily intended for treatment of patients (but also animals) with pain, injuries or degeneration in the brain and/or the spinal cord; as a research tool in studies of neuronal network function, and plasticity, development and aging of the nervous system; as an interface in brain-computer communication enabling prosthesis control or control of skeletal muscle; and for control of endocrine and exocrine organ function.

Clinical Use.

The electrode bundle of the invention may serve to aid patients with brain or spinal damage of various kind by recording signals from remaining neurons in case of e.g. stroke or degenerative disease and/or to stimulate neurons to compensate for lost functions. Similar uses are possible in animals. For instance, the electrode bundle can be used to relieve pain by stimulation of analgesic brain stem centres, such as nuclei in the periaqueductal grey substance; to relieve or decrease tremor in Parkinson's disease, choreatic and other involuntary movements by stimulation within the basal ganglia or associated nuclei; to boost memory by stimulation of cholinergic and/or monoaminergic nuclei in case of Alzheimer's disease or other degenerative diseases; to control mood, aggression, anxiety, phobia, affect, sexual over-activity, impotence, eating disturbances by stimulation of limbic centres or other brain areas; to rehabilitate patients after stroke or damage of the brain/spinal cord by stimulation of remaining connections in cortex cerebri or descending motor pathways; to re-establish control of spinal functions such as bladder and bowel emptying after spinal cord injury by stimulating relevant parts in the spinal cord; to control spasticity by stimulation of inhibitory supraspinal descending centres or appropriate cerebellar areas.

The electrical bundle may be used for electrolytic leasioning of specific tissue sites by passing electrical currents through the tissue. In such case the intensity of the current administered via the electrode bundle is chosen to be adequate for accomplishing cell death in a tissue volume adjacent to the front end of the electrode bundle. For example, the electrode bundle can be used to lesion tumours or CNS sites that have developed abnormal activity after e.g. an insult or a degenerative disease.

Examples of combined recording and stimulation: monitoring of epileptic attacks by electrodes implanted into the epileptic focus coupled with a system for administration of antiepileptic drugs and/or electrical pulses; compensating for lost connections in the motor system by recording central motor commands, and stimulating the executive parts of the motor system distal of the lesions; selecting a site producing abnormal electrical activity by recording neuronal activity at the site, followed by lesioning the tissue at the site by administration via the electrode bundle of a current of adequate strength for an adequate period of time.

Use as a Research Tool.

The electrode bundle of the invention may be used for studies of normal as well as abnormal functions of the brain and the spinal cord and/or the peripheral nervous system (PNS). In such studies it is necessary to record neuronal activity and to simultaneously interact with the undisturbed CNS or PNS. For this purpose, the electrode bundle(s) of the invention is implanted in the CNS and/or PNS for a long time.

Use as Interface for Communication with Computers and Neuroprosthesis.

In patients with damage to the peripheral nervous system, it can be useful to record command signals from the CNS. These signals can be interpreted by computer programs and used to control neuroprosthesis such as artificial hands or feet, and also to control stimulation of muscles and organs such as the bladder and the bowel.

Control of the Function of Endocrine and Exocrine Organs.

In patients with deficient hormone secretion or regulation, the electrode bundle of the invention may be used to control the secretion of hormones from exocrine or endocrine organs.

The invention claimed is:

1. Electrode bundle for implantation by insertion into soft tissue comprising two or more electrically independent electrodes each having a front and rear end aligned in parallel, the front ends forming the front end of the bundle and the rear ends forming the rear end of the bundle, each electrode comprising (a) an oblong electrically conducting electrode element having a front end and a rear end, (b) an anchoring element having a free end and a second end joined to the electrode element at the front end or a portion thereof intermediate between the front end and the rear end, the anchoring element forming an angle $\alpha$ with the electrode element of from 0° to 60° and extending in the direction of the rear end thereof, (c) a plurality of electrical conductors each of which is attached to a different one of said two or more electrodes at the rear end thereof, and (d) an element bundling the electrodes disposed between the anchoring element and the rear end.

2. The electrode bundle of claim 1, wherein the free end of the anchoring element is pointed.

3. The electrode bundle of claim 1, wherein the electrode element and the anchoring element is one piece.

4. The electrode bundle of claim 3, wherein the piece is selected from the group consisting of metal wire, carbon fibre and ceramic or glass fibre having an electrically conducting coat.

5. The electrode bundle of claim 4, wherein the electrically conducting coat is metallic.

6. The electrode bundle of claim 1, wherein the attachment is solder, weld, or an electrically conducting glue.

7. The electrode bundle of claim 1, further comprising an insulating coat disposed to cover the electrodes, except for a portion extending from the free end of the anchoring element.

8. The electrode bundle of claim 1, wherein the anchoring element or the anchoring element and the electrode element are of a resilient material.

9. The electrode bundle of claim 1, wherein the anchoring element is curved.

10. The electrode bundle of claim 9, further comprising adhesive disposed to adhesively mount the curved anchoring element in a resiliently strained state in abutment with the electrode element.

11. The electrode bundle of claim 10, wherein the adhesive is soluble or swellable in water.

12. The electrode bundle of claim 1, wherein the anchoring element comprises a hinge joined at a point near to an end of the hinge to the electrode element.

13. The electrode bundle of claim 1, wherein the anchoring element comprises memory metal in a strained state seeking, when warmed to body temperature, to adopt a configuration at which at least part of the anchoring element is more distant from the electrode element.

14. The electrode bundle of claim 1, wherein the bundling element comprises a sleeve or ring.

15. The electrode bundle of claim 1, further comprising a cylindrical core of a non-conducting material having a periphery at which the electrodes are disposed with their electrode elements.

16. The electrode bundle of claim 15, wherein the anchoring elements extend in a generally radial direction in respect of the core.

17. The electrode bundle of claim 1, further comprising a sensing electrode for control of insertion depth of the bundle co-operatively connected to the bundle, the sensing electrode being slidingly disposed in an axial bore of the core and of a length exceeding that of the bundle.

18. The electrode bundle of claim 1, further comprising a flat non-conductive support having a face, and wherein the electrodes are disposed on the face of a flat non-conductive support.

19. The electrode bundle of claim 18, wherein the flat non-conductive support face has parallel opposing edges, and the anchoring elements are disposed in parallel with parallel opposite edges of said face of the support.

20. The electrode bundle of claim 19, wherein the anchoring elements are disposed in a mirroring fashion in respect of an axis centred in respect said edges.

21. A stack comprising at least two adjacent electrode bundles of claim 18 and further comprising a distance element disposed between the adjacent bundles.

22. The stack of claim 21, having electrical shielding disposed between the adjacent electrode bundles of the stack.

23. The stack of claim 22, wherein the electrical shielding comprises a metal sheet or net or a metallic layer and is disposed on the face of the support.

24. The electrode bundle of claim 1 further comprising a recording device operatively connected thereto.

25. The electrode bundle of claim 1 further comprising an electrical source operatively connected thereto.

* * * * *

UNITED STATES PATENT AND TRADEMARK OFFICE
CERTIFICATE OF CORRECTION

PATENT NO. : 8,457,762 B2  
APPLICATION NO. : 11/543825  
DATED : June 4, 2013  
INVENTOR(S) : Jens O. Schouenborg Page 1 of 1

It is certified that error appears in the above-identified patent and that said Letters Patent is hereby corrected as shown below:

\*\*On the Title Page, Item (73) Assignee should read: Neuronano AB\*\*

Signed and Sealed this  
Eighth Day of April, 2014

Michelle K. Lee  
*Deputy Director of the United States Patent and Trademark Office*